US009468462B2

(12) United States Patent
Rosenbaum et al.

(10) Patent No.: US 9,468,462 B2
(45) Date of Patent: Oct. 18, 2016

(54) CATHETER AND SUPPORT CANNULA ASSEMBLY

(71) Applicant: Cook Medical Technologies, LLC, Bloomington, IN (US)

(72) Inventors: Joanna L. Rosenbaum, Bloomington, IN (US); James A. Taylor, Bloomington, IN (US); Benjamin T. Biltz, Spencer, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 410 days.

(21) Appl. No.: 14/079,102

(22) Filed: Nov. 13, 2013

(65) Prior Publication Data

US 2014/0142542 A1 May 22, 2014

Related U.S. Application Data

(60) Provisional application No. 61/728,099, filed on Nov. 19, 2012.

(51) Int. Cl.
*A61M 25/00* (2006.01)
*A61B 17/34* (2006.01)
(Continued)

(52) U.S. Cl.
CPC ....... *A61B 17/3421* (2013.01); *A61B 17/3415* (2013.01); *A61M 25/0102* (2013.01); *A61M 25/065* (2013.01); *A61M 27/00* (2013.01); *A61M 25/007* (2013.01); *A61M 25/0074* (2013.01);
(Continued)

(58) Field of Classification Search
CPC ............. A61M 25/04; A61M 25/007; A61M 25/0606; A61M 25/0102; A61M 2025/0163; A61M 25/06; A61B 17/3415; A61B 17/3417
See application file for complete search history.

(56) References Cited

U.S. PATENT DOCUMENTS 918,437 A 4/1909 Genung
3,419,010 A 12/1968 Williamson
(Continued)

FOREIGN PATENT DOCUMENTS

DE 32 48 067 A1 12/1982
DE 20 2004 008 827 U1 9/2004
(Continued)

OTHER PUBLICATIONS

Extended European Search Report for EP 13 19 2921.8 dated Jan. 27, 2014.
(Continued)

*Primary Examiner* — Aarti B Berdichevsky
(74) *Attorney, Agent, or Firm* — Brinks Gilson & Lione (57) ABSTRACT

A system may include a catheter and a support cannula within the catheter. The catheter may include a tapered tip and a body extending proximally therefrom. The catheter tip may have a smaller inner diameter than the catheter body. The support cannula may include a tip disposed within the catheter tip such that the support cannula tip does not extend distally beyond the catheter distal end and a support segment extending proximally from the support cannula tip and disposed within the catheter body such that the catheter body remains in a non-stretched configuration. An outer diameter of the cannula tip may correspond to the inner diameter of the catheter tip. An outer diameter of the support segment may correspond to the inner diameter of the catheter body. The support segment may extend proximally to at least a proximal end of a perforated segment of the catheter body.

15 Claims, 7 Drawing Sheets

(51) Int. Cl.
*A61M 25/01* (2006.01)
*A61M 27/00* (2006.01)
*A61M 25/06* (2006.01)
*A61M 25/04* (2006.01)
*A61M 29/00* (2006.01)

(52) U.S. Cl.
CPC .............. *A61M 25/04* (2013.01); *A61M 29/00* (2013.01); *A61M 2025/0163* (2013.01); *A61M 2025/0681* (2013.01)

(56) References Cited

U.S. PATENT DOCUMENTS

| | | | |
|---|---|---|---|
| 3,459,189 A | 8/1969 | Alley et al. | |
| 3,860,006 A | 1/1975 | Patel | |
| 3,946,741 A | 3/1976 | Adair | |
| 3,993,079 A | 11/1976 | De Gatztanondo | |
| 4,160,450 A | 7/1979 | Doherty | |
| 4,571,239 A | 2/1986 | Heyman | |
| 4,610,657 A | 9/1986 | Densow | |
| 4,808,158 A | 2/1989 | Kreuzer et al. | |
| 4,986,814 A * | 1/1991 | Burney ................ | A61M 25/01 604/164.11 |
| 5,120,317 A | 6/1992 | Luther | |
| 5,205,830 A | 4/1993 | Dassa et al. | |
| 5,215,528 A | 6/1993 | Purdy et al. | |
| 5,356,390 A | 10/1994 | Erskine | |
| 5,382,238 A | 1/1995 | Abrahamson et al. | |
| 5,409,462 A | 4/1995 | Ross | |
| 5,489,269 A * | 2/1996 | Aldrich .............. | A61B 17/3415 604/540 |
| 5,669,883 A | 9/1997 | Scarfone et al. | |
| 6,454,740 B1 | 9/2002 | Mody | |
| 7,967,770 B2 | 6/2011 | Li et al. | |
| 7,967,787 B2 | 6/2011 | Nagata et al. | |
| 8,137,316 B2 | 3/2012 | Haarala et al. | |
| 2007/0083161 A1 | 4/2007 | Briscoe et al. | |
| 2007/0112302 A1 | 5/2007 | Yu | |
| 2008/0125756 A1 | 5/2008 | Dicarlo et al. | |
| 2010/0049171 A1 | 2/2010 | McQueen et al. | |
| 2011/0213316 A1 | 9/2011 | Ibrahim et al. | |
| 2012/0078095 A1 | 3/2012 | Heck | |

FOREIGN PATENT DOCUMENTS

| | | |
|---|---|---|
| EP | 0 245 211 A1 | 2/1987 |
| EP | 0347 170 A1 | 6/1989 |
| EP | 1 872 819 A1 | 2/2008 |
| WO | WO 83/00429 | 2/1983 |

OTHER PUBLICATIONS

Communication pursuant to Article 94(3) EPC regarding application examination, dated Feb. 11, 2015, 6 pp.

* cited by examiner

CATHETER AND SUPPORT CANNULA ASSEMBLY

CROSS-REFERENCE TO RELATED APPLICATIONS

This application claims priority from U.S. Provisional Application No. 61/728,099, filed on Nov. 19, 2012, the entirety of which is hereby fully incorporated by reference herein.

TECHNICAL FIELD

This disclosure relates generally to medical devices. More specifically, this disclosure relates to drainage/infusion catheters for percutaneous placement within a body cavity to drain a fluid from the body cavity and/or to infuse a fluid into the body cavity.

BACKGROUND

The use of catheters for draining excess or infected body fluids from a body cavity or for infusing medication into a body cavity is well known. One use of the catheter may be to drain excess fluid. For example, the catheter may be used to drain urine from the kidney when there is an obstruction in the ureter. Another use of the catheter may be to drain fluid from an infected collection. For example, the catheter may be used to drain pus from an abdominal abscess. Once in position, the flexible distal portion at the end of the catheter may be altered to help to maintain the flexible distal portion within the body cavity. For example, one or more loops may be imparted at the distal flexible end of the catheter. These loops may be much larger than the hole through which the catheter is inserted. This may help to retain the catheter in the body cavity, which may help to prevent inadvertent removal of the catheter from the body cavity. Excess or infected fluid may enter a port or hole in the tubular member of the catheter and be withdrawn from the body cavity by aspiration or by gravity.

Typically, inserting the drainage catheter into the body cavity is done with the aid of an insertion tool, such as a stiffening cannula. The stiffening cannula may be inserted into the drainage catheter to support the drainage catheter and/or to at least partially straighten the loops at the distal flexible end of the catheter for placement in the body cavity. Typically, the stiffening cannula has a cylindrical shape with an outer diameter that is either larger than the inner diameter of the tip of the drainage catheter (which may be tapered) or smaller than the inner diameter of the body of the drainage catheter. A large gauge stiffening cannula may be unable to fit within the tip of the drainage catheter, which may result in a failure to straighten and/or support the tip of the drainage catheter. A small gauge stiffening cannula may not fully contact the inner surface of the body of the drainage catheter, which may result in a failure to support the body of the catheter. Failure to support and/or straighten the drainage catheter may result in damage to the drainage catheter caused by buckling and/or puncturing of the drainage catheter during insertion of the drainage catheter into the body cavity.

SUMMARY

The present embodiments provide a drainage/infusion catheter for percutaneous placement within a body cavity to drain a fluid from the body cavity and/or to infuse a fluid into the body cavity.

In one example, a system may include a catheter and an elongate tubular support cannula. The catheter may include an elongate tubular member including a proximal end, a distal end, a lumen extending longitudinally within the catheter, a tapered tip positioned at the distal end of the catheter, and a body extending proximally from the tip. The tip of the catheter may have an inner diameter that is smaller than an inner diameter of the body of the catheter. The support cannula may be slidably received within the lumen of the catheter. The support cannula may include a proximal end, a distal end, a lumen extending longitudinally within the support cannula, a tip positioned at the distal end of the support cannula and disposed within the tip of the catheter such that the tip of the support cannula does not extend distally beyond the distal end of the catheter, and a support segment extending proximally from the tip of the support cannula and disposed within the body of the catheter such that the body of the catheter remains in a non-stretched configuration. The tip of the support cannula may have an outer diameter corresponding to the inner diameter of the tip of the catheter. The support segment may have an outer diameter corresponding to the inner diameter of the body of the catheter. The body of the catheter may include a perforated segment including an aperture disposed in the catheter and in fluid communication with the lumen of the catheter. The support segment of the support cannula may extend from the tip of the support cannula to at least a position longitudinally adjacent to a proximal end of the perforated segment.

In another example, a system may include a catheter, an elongate tubular support cannula, and an elongate needle. The catheter may include an elongate tubular member including a proximal end, a distal end, a catheter lumen extending longitudinally within the catheter, a catheter body, and a catheter tip extending distally from the catheter body. The catheter tip may include a tapered outer surface and an inner diameter that is smaller than an inner diameter of the catheter body. The support cannula may be slidably received within the catheter lumen and include a proximal end, a distal end, a cannula lumen extending longitudinally within the support cannula, a support segment disposed within the catheter body, and a cannula tip extending distally from the support segment and disposed within the catheter tip. The support segment may include an outer diameter that is substantially constant along a length of the support segment and corresponds to the inner diameter of the catheter body. The cannula tip may include an outer diameter that is smaller than the outer diameter of the support segment and corresponds to the inner diameter of the catheter tip. The needle may be slidably received within the cannula lumen and include a proximal end, a distal end, and a sharpened tip positioned at the distal end of the needle and disposed distal of the distal end of the catheter. The catheter body may include a perforated segment including a plurality of apertures in fluid communication with the catheter lumen and longitudinally spaced from one another along a length of the perforated segment. The support segment may be disposed within the perforated segment of the catheter body and may extend proximally from the cannula tip to at least a position longitudinally aligned with a proximal end of the perforated segment.

In another example, a method for percutaneous placement of a catheter into a body cavity may include providing the catheter and a support cannula. The catheter may include a catheter body and a catheter tip extending distally from the catheter body. The catheter tip may have an inner diameter that is smaller than an inner diameter of the catheter body.

The support cannula may include a support segment and a cannula tip extending distally from the support segment. The support segment may have an outer diameter corresponding to the inner diameter of the catheter body. The cannula tip may have an outer diameter corresponding to the inner diameter of the catheter tip. The method may include positioning the support cannula within a lumen of the catheter. The support segment may be in contact with an inner surface of a perforated segment of the catheter body along substantially an entire length of the perforated segment. The perforated segment may include a plurality of apertures in fluid communication with the lumen of the catheter and longitudinally spaced from one another along the length of the perforated segment. The cannula tip may be in contact with an inner surface of the catheter tip. A distal end of the support cannula may be disposed within the catheter tip. The method may include advancing the catheter and the support cannula distally through a puncture in a body tissue.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

DETAILED DESCRIPTION OF THE DRAWINGS AND THE PRESENTLY PREFERRED EMBODIMENTS

Detailed embodiments of the present invention are disclosed herein. It is understood, however, that the disclosed embodiments are merely exemplary of the invention, which may be embodied in various and alternative forms. The figures are not necessarily to scale, and some figures may be configured to show the details of a particular component. Therefore, specific structural and functional details disclosed herein are not to be interpreted as limiting, but merely as a representative basis for the claims and for teaching one skilled in the art to practice the present invention.

In the present disclosure, the term "proximal" refers to a direction that is generally toward a physician during a medical procedure, while the term "distal" refers to a direction that is generally toward a target site within a patient's anatomy during a medical procedure.

Various medical devices for introduction and/or implantation in a body cavity are disclosed herein. Preferred embodiments relate to a drainage/infusion catheter for percutaneous placement within a body cavity to drain a fluid from the body cavity and/or to infuse a fluid into the body cavity. Such devices may be used in performing medical procedures such as, for example, cystostomy, nephrostomy, abscess drainage, biliary drainage, endopyelotomy, pericardial drainage, pleural drainage, spinal drainage, tracheotomy, enteral or tube feeding, urethral drainage, sinus drainage, or any other medical procedure involving drainage and/or introduction of a fluid from and/or into a body cavity. The body cavity may include any space within a body. For example, the body cavity may include a bladder, a kidney, an abscess, a bile duct, a ureteropelvic junction, a body vessel (e.g., a blood vessel), or any other space within a body. The medical devices are described with respect to an exemplary loop catheter embodiment for drainage of a fluid from a body cavity. However, this disclosure is not so limited, and may be applicable to other types of drainage and/or infusion devices. For example, the medical device may include a Foley catheter, a malecot catheter, a balloon catheter, an angled-tip catheter, or a straight catheter.

Figure 1:
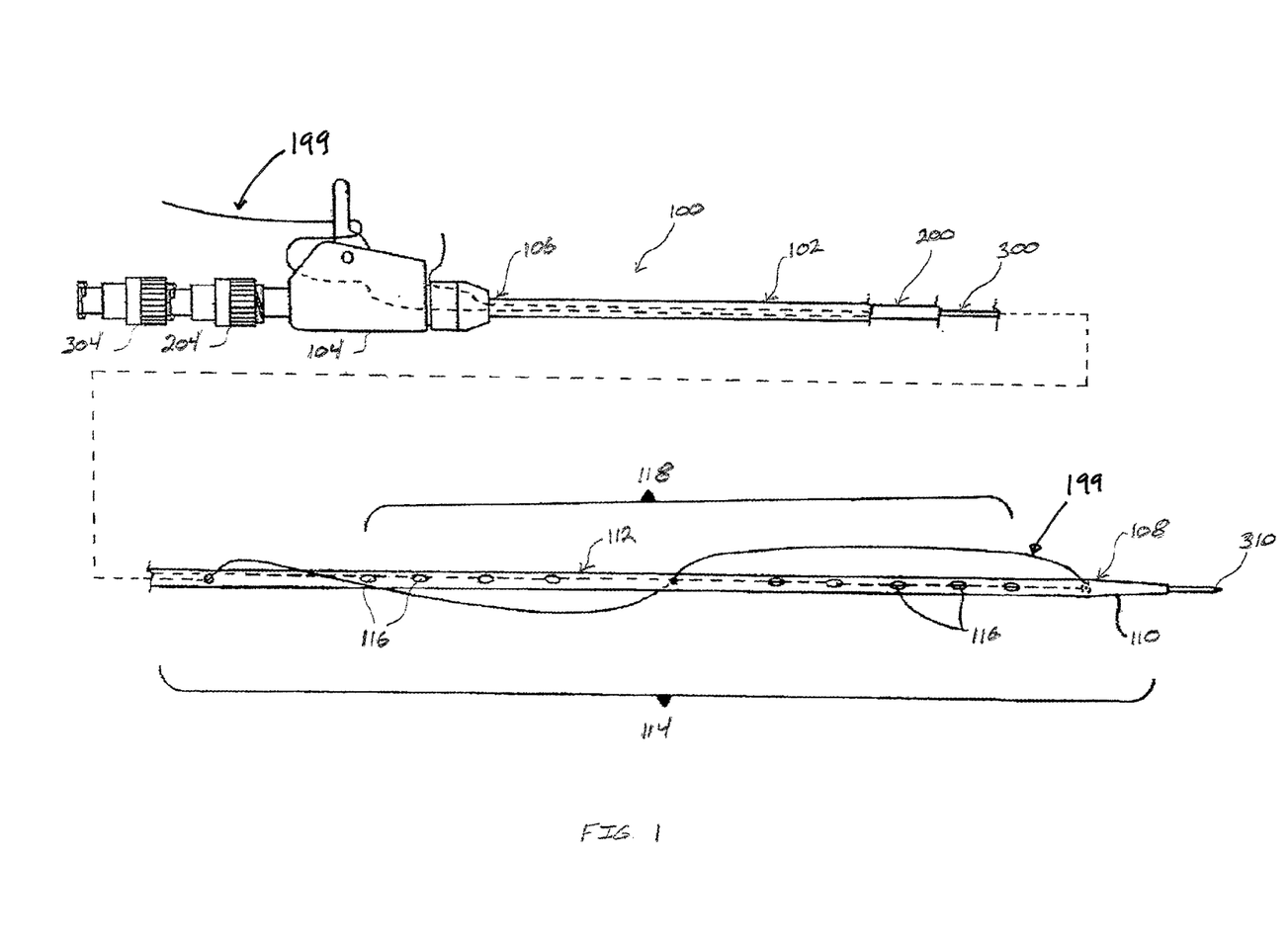
FIG. 1 illustrates one example of a system for draining a fluid from a body cavity and/or infusing a fluid into the body cavity including a catheter, a support cannula, and a needle.

FIG. 1 illustrates one example of a system for draining a fluid (e.g., excess fluid and/or infected fluid) from a body cavity and/or infusing a fluid (e.g., medication) into the body cavity. The system may include a catheter 100, a support cannula 200, and/or a needle 300. The support cannula 200 may be received within the catheter 100 to support at least a portion of the catheter as further described below. The needle 300 may be received within the support cannula 200 to aid in percutaneous placement of the catheter 100 as further described below.

At least a portion of the catheter 100 may be placed within a body cavity to drain a fluid from the body cavity and/or to infuse a fluid into the body cavity. In one example, the catheter 100 may be similar to the catheter described in U.S. Pat. No. 6,454,740 to Mody, which is incorporated by reference herein in its entirety. In other examples, the catheter 100 may have any other suitable configuration for placement within a body cavity. To that end, the catheter 100 may include an elongate tubular member 102. A hub 104 may be positioned at the proximal end of the catheter 100. The tubular member 102 may include a proximal end 106 adjacent to the hub 104 and a distal end 108 positioned opposite the proximal end. The catheter 100 may include a tip 110 positioned at the distal end 108. The tip 110 may be configured as a pointed or tapered end of the tubular member 102 as shown in FIG. 1. In other words, the tip 110 may be configured as a dilator tip to aid in dilating a puncture in a body tissue during percutaneous placement of the catheter 100 as further described below. The catheter 100 may include a body 112 extending proximally from the tip 110. In other words, the tubular member 102 of the catheter 100 may include the body 112 and the tip 110 extending distally from the body 112. A lumen may extend longitudinally within the catheter 100. For example, the lumen of the catheter 100 may extend from a proximal end opening at the hub 104 to a distal end opening at the tip 110. Fluid may be passed out of and/or into the body cavity via the lumen of the catheter 100. Additionally, or alternatively, the support cannula 200 may be received within the lumen of the catheter 100 to provide support to the catheter during placement of the catheter within the body cavity as further described below.

Figure 2:
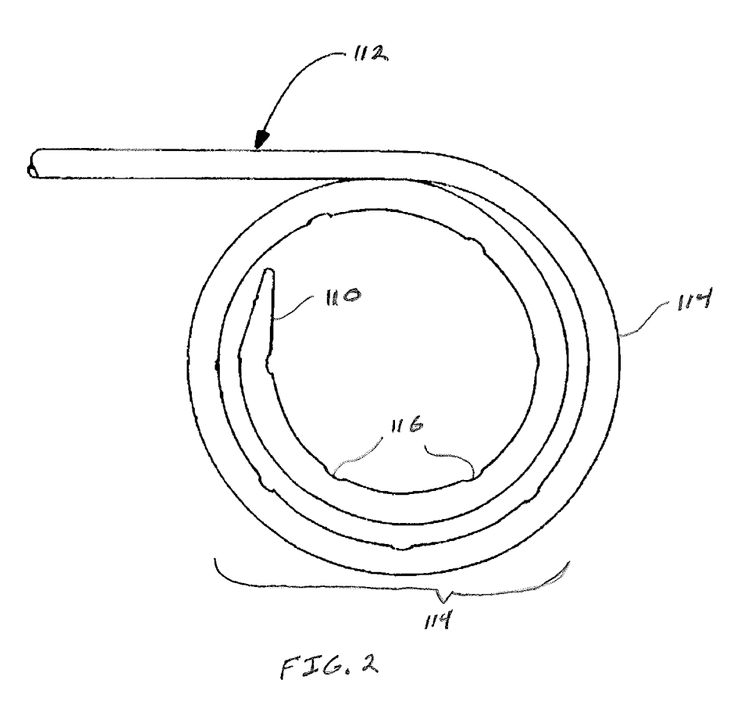
FIG. 2 illustrates a distal portion of the catheter of FIG. 1 in a deployed configuration.

The tubular member 102 may include a retaining segment 114 positioned near the distal end 108 of the catheter 100. In one example, the retaining segment 114 may be configured as a segment of the catheter 100 extending proximally from the tip 110. In other words, the retaining segment 114 may include a portion of the body 112 of the tubular member 102 positioned near the distal end 108 of the catheter 100. In another example, the retaining segment 114 may include the distal portion of the body 112 and the tip 110. The retaining segment 114 may be configured to retain the catheter 100 in place within the body cavity as further described below. To that end, the retaining segment 114 may be movable between a delivery configuration and a deployed configuration. In the delivery configuration, the retaining segment 114 may be substantially linear or rod-like as shown in FIG. 1. In other words, the longitudinal axis of the tubular member 102 may be substantially linear along the retaining segment 114. In the deployed configuration, the retaining segment 114 may be substantially non-linear as shown in FIG. 2. For example, the retaining segment 114 may include one or more loops formed in the tubular member 102 as shown in FIG. 2.

Additionally, or alternatively, in the delivery configuration, the retaining segment may have a delivery width (e.g., the diameter of the catheter). In the deployed configuration, the retaining segment may have a deployed width (e.g., the diameter of the loop, inflated balloon, expanded malecot, or other retaining mechanism) that is larger than the delivery width. The larger deployed width may be achieved, for example, by forming one or more loops as shown in FIG. 2, inflating a balloon, expanding a malecot or barb, or any other suitable method of enlarging the diameter of the retaining segment.

In one example, the retaining segment 114 may be biased toward the deployed configuration. In other words, the retaining segment 114 of the tubular member 102 may be preformed such that, in a relaxed condition, with the support cannula 200 and the needle 300 removed, the loops (or other retaining mechanism) are naturally formed. The support cannula 200 and/or the needle 300 may be received within the retaining segment 114 to retain the retaining segment in the delivery configuration for placement of the catheter 100 as further described below.

Although FIG. 2 illustrates the retaining segment 114 as including two loops, this disclosure is not so limited. In other examples, the retaining segment may include any number of loops (e.g., one, three, four, or more). Additionally, or alternatively, the retaining segment, in the deployed configuration, may have any other shape (e.g., J-shaped, helical, zig-zag, angled tip, or any other shape) configured to retain the catheter 100 in place within the body cavity. Additionally, or alternatively, the retaining segment may include a barb, a malecot, a balloon, or any other suitable retaining mechanism configured to retain the catheter in place within the body cavity.

The catheter 100 may include at least one aperture 116 disposed in the tubular member 102. In one example, the catheter 100 may include a plurality of apertures 116 as shown in FIGS. 1-2. Each aperture 116 may extend through the sidewall of the tubular member 102 such that the lumen of the catheter 100 is in fluid communication with a point external of the catheter through the aperture. The plurality of apertures 116 may extend along a perforated segment 118 of the tubular member 102. The perforated segment 118 may extend longitudinally from a most proximal aperture 116 to a most distal aperture. The perforated segment 118 may be a portion of the body 112 of the tubular member 102 positioned near the distal end 108 of the catheter. Additionally, or alternatively, the perforated segment 118 may be at least partially coextensive with the retaining segment 114. The apertures 116 may be longitudinally spaced from one another along the perforated segment 118. In one example, each aperture 116 may be longitudinally spaced from an adjacent aperture by a distance of about 0.5 in.

Each aperture may be configured as a drainage/infusion port. To that end, when the catheter 100 is placed within the body cavity, excess fluid may migrate into the apertures 116 and travel proximally within the tubular member 102 and out through the hub 104. The excess fluid may flow by the force of gravity or may be extracted using a syringe or other device. Additionally, or alternatively, a fluid may be introduced into the catheter through the hub 104 and flow distally within the tubular member 102 and out through the apertures 116. In this manner, the fluid may be infused into the body cavity. In one example, the fluid may be a medication which may assist in treating the patient. For example, the fluid may be a medication which may assist in breaking up material contained within the body cavity so that the material may be withdrawn from the body cavity using the catheter 100.

In one example, the plurality of apertures 116 may be aligned with one another with respect to a circumference of the tubular member 102. In other words, the plurality of apertures 116 may be radially aligned with one another as shown in FIGS. 1-2. The plurality of apertures may be positioned on one side of the perforated segment 118 such that, in the deployed configuration, the apertures will not be blocked by an adjacent loop formed in the tubular member 102. Additionally, or alternatively, the plurality of apertures 116 may include two or more sets of apertures. In one example, the plurality of apertures 116 may include two sets of apertures positioned opposite one another with respect to the circumference of the tubular member 102. In other words, the two sets of apertures may be diametrically opposed with respect to the tubular member 102. In this manner, the plurality of apertures 116 may include one set of apertures positioned on each side of the loops formed in the tubular member 102 in the deployed configuration. In other examples, the apertures 116 may be positioned at any other longitudinal and/or circumferential position along the tubular member 102. For example, the apertures may be positioned in a linear arrangement, a helical arrangement, a random arrangement, or any other pattern or arrangement.

The catheter 100 may include an actuating mechanism to aid in moving the retaining segment 114 between the delivery configuration and the deployed configuration. In one example, the actuating mechanism may include a thread 199 extending from the hub 104 to a point at the distal end 108 of the catheter 100 and back to the hub as shown in FIG. 1 and described in U.S. Pat. No. 6,454,740 to Mody, which is incorporated by reference herein in its entirety. The thread 199 may extend through a plurality of holes in the tubular member such that pulling an end of the thread 199 proximally relative to the tubular member 102 pulls the retaining segment 114 into the deployed configuration. In other examples, the actuating mechanism may include an actuating member which may be positioned at the retaining segment 114 to bias the retaining segment toward the deployed configuration. The actuating member may include, for example, a wire or a tube formed from a superelastic or shape memory material. In other examples, the retaining segment 114 may be preformed so that, in a relaxed condition, the retaining segment tends to move toward the deployed configuration.

Figure 3:
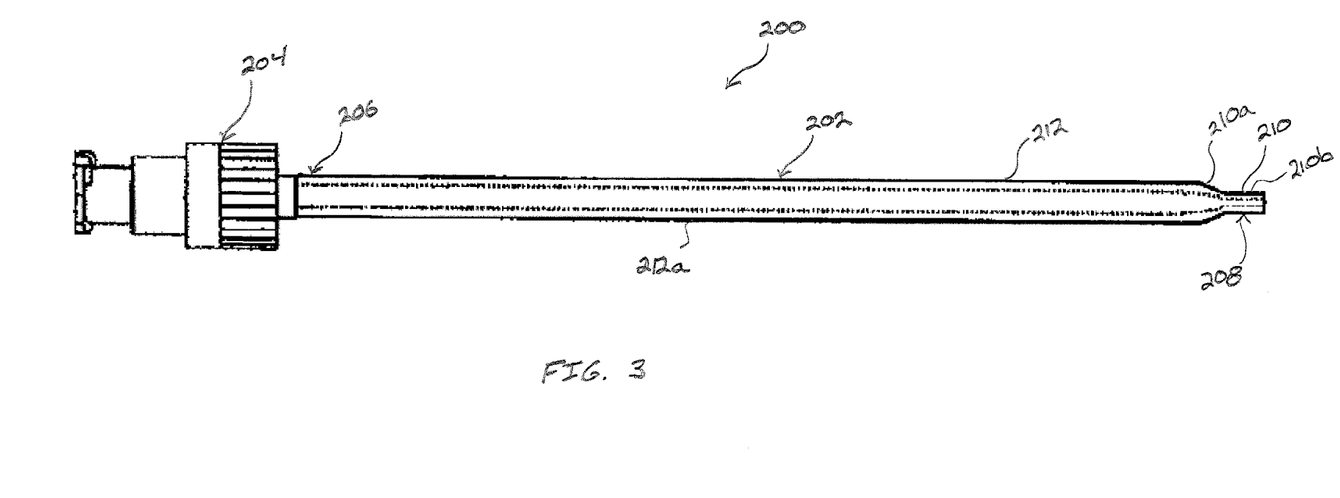
FIG. 3 illustrates one example of a support cannula.

FIG. 3 illustrates one example of the support cannula 200. The support cannula may include an elongate tubular member 202. A hub 204 may be positioned at the proximal end of the support cannula 200. The tubular member 202 may include a proximal end 206 adjacent to the hub 204 and a distal end 208 positioned opposite the proximal end. The support cannula 200 may include a tip 210 positioned at the distal end 208. The support cannula 200 may include a body 212 extending proximally from the tip 210. In other words, the tubular member 202 of the support cannula 200 may include the body 212 and the tip 210 extending distally from the body 212. A lumen may extend longitudinally within the support cannula 200. For example, the lumen of the support cannula 200 may extend from a proximal end opening at the hub 204 to a distal end opening at the tip 210.

The tubular member 202 of the support cannula 200 may be received within the lumen of the catheter 100 as shown in FIG. 1. In one example, the length of the tubular member 202 may be shorter than or substantially equal to the length of the catheter 100 (e.g., the distance from the proximal end opening of the hub 104 to the distal end opening of the tip 110). In this manner, the tip 210 of the support cannula 200 may be disposed within the catheter 100 as shown in FIG. 1. In one example, the distal end of the tip 210 of the support cannula 200 (e.g., the distal end opening of the support cannula) may be longitudinally aligned with the distal end of the tip 110 of the catheter 100 (e.g., the distal end opening of the catheter). Additionally, or alternatively, the hub 204 of the support cannula 200 may be engaged with the hub 104 of the catheter 100. In one example, the hub 204 of the support cannula 200 may be coupled to the hub 104 of the catheter 100 to couple the support cannula and the catheter to one another for delivery of the catheter to the body cavity. For example, the hub 204 of the support cannula 200 may be threadably engaged with the hub 104 of the catheter to couple the support cannula and the catheter to one another. In another example, the hub 204 of the support cannula 200 and the hub 104 of the catheter 100 may include interlocking features (e.g., a notch and slot mechanism or a snap fit mechanism) which may engage one another to couple the support cannula and the catheter to one another. In other examples, the support cannula and the catheter may be coupled to one another by any other suitable coupling mechanism.

The tip 210 of the support cannula 200 may have a smaller outside diameter than the body 212 as shown in FIG. 3. In one example, the tip 210 may include a tapered portion 210a adjacent to the body 212. An end portion 210b may extend distally from the tapered portion 210a. The tapered portion 210a may form a smooth transition between the larger diameter of the body 212 and the smaller diameter of the tip 210 (e.g., at the end portion 210b). The outer diameter of the end portion 210b may be substantially constant from the tapered portion to the distal end of the tip 210. In one example, the tapered portion 210a may have a substantially frustoconical shape. Additionally, or alternatively, the end portion 210b may have a substantially cylindrical shape. In other examples, the tapered portion and the end portion may have any suitable size and/or shape. In other examples, the tapered portion 210a or the end portion 210b may be omitted. For example, the tapered portion 210a may be omitted such that the end portion 210b extends from the proximal end to the distal end of the tip 210. The outer diameter of the tubular member 202 may transition in a stepwise manner from the larger outer diameter of the body 212 to the smaller outer diameter of the tip 210. In another example, the end portion 210b may be omitted such that the tapered portion 210a extends from the proximal end to the distal end of the tip 210. The outer diameter of the tip 210 may taper from the proximal end to the distal end of the tip 210.

In any of the examples described herein, the tip 210 and the body 212 of the support cannula 200 may be formed as a unitary structure or as separate structures joined to one another to form the support cannula. For example, the tip 210 may be formed at the distal end of a substantially cylindrical support cannula using any suitable method known in the art such as, for example, swaging, metal spinning, grinding, deep drawing, drilling, or any other method. In another example, the tip 210 may be attached to the body 212 using any suitable method known in the art such as, for example, soldering, gluing, welding, or any other method.

The support cannula 200 may be received within the catheter 100 to support the catheter during placement within the body cavity as further described below. To that end, the body 212 of the support cannula 200 may be sized and shaped to be received within the body 112 of the catheter 100. A support segment of the body 112 may be positioned adjacent to the perforated portion 118 of the catheter 100 as further described below. Additionally, or alternatively, the tip 210 of the support cannula 200 may be sized and shaped to be received within the tip 110 of the catheter 100.

Figure 4:
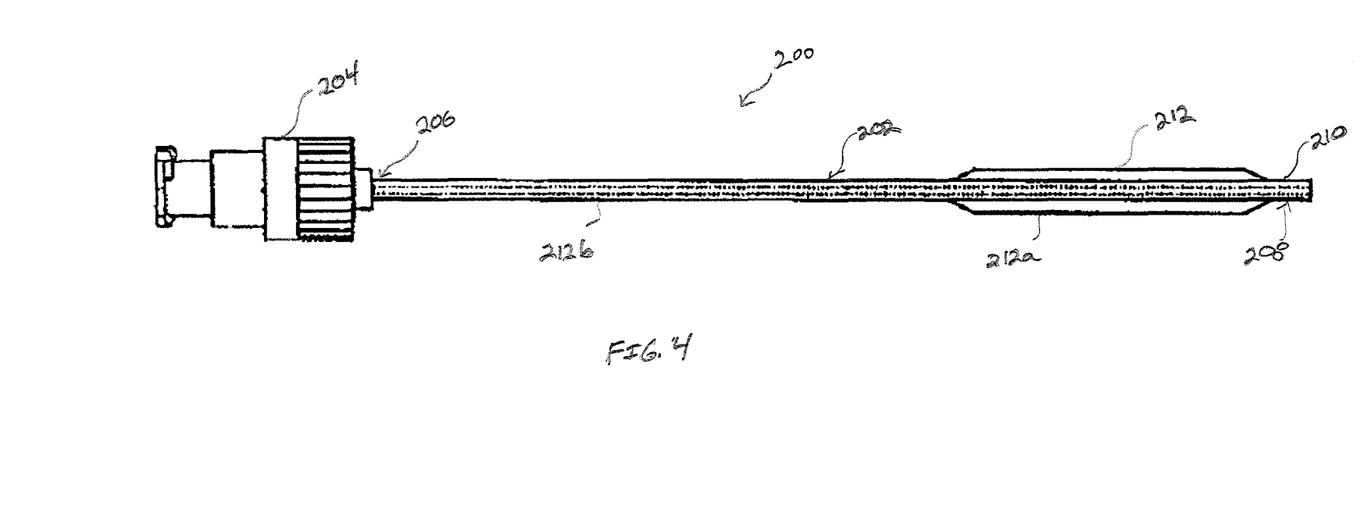
FIG. 4 illustrates another example of a support cannula.

In one example, substantially the entire body 212 may be configured as a support segment 212a to support the body 112 of the catheter 100. To that end, the body 212 of the support cannula 200 may have a substantially constant outside diameter along the length of the body from the proximal end of the tubular member 202 to the tip 210 as shown in FIG. 3. In another example, the body 212 of the support cannula 200 may include the support segment 212a and an extension segment 212b as shown in FIG. 4. The support segment 212a may be positioned near the distal end 208 of the support catheter 200. In one example, the support segment 212a may be positioned adjacent to the tip 210 as shown in FIG. 4. The extension segment 212b may be positioned proximal of the support segment 212a. In one example, the extension segment 212b may extend between the hub 204 and the support segment 212a. In other words, the extension segment 212b may be positioned between the hub 204 and the support segment 212a. In this manner, the support segment 212a may be spaced longitudinally from the hub 204 for proper alignment with the catheter 100 (e.g., with the perforated segment 118) as further described below. The support segment 212a and the extension segment 212b may have any suitable lengths. In one example, the support segment 212a may have a length of between about 2 cm and about 7 cm, typically about 5 cm. Additionally, or alternatively, the extension segment 212b may have a length of between about 16 cm and about 47 cm, typically about 31.5 cm. The length of the support segment 212a and/or the extension segment 212b may depend on factors including, for example, the length of the catheter, the length of the perforated segment, the length of the retaining segment, or the anatomy that is targeted in a procedure.

The support segment 212a may have a larger outside diameter than the tip 210 as described above with reference to FIG. 3. The extension segment 212b may have a smaller outside diameter than the support segment 212a as shown in FIG. 4. The outer surface of the extension segment 212b may include a tapered portion that tapers from the smaller outside diameter of the extension segment to the larger outside diameter of the support segment 212a. In one example, the extension segment 212b may have a diameter that is substantially the same as the tip 210 (e.g., the end portion 210b). To that end, the extension segment 212b and the tip 210 may be formed from a substantially continuous first tubular member. The support segment 212a may be formed from a second tubular member having a larger diameter than the first tubular member. The second tubular member may be positioned around the first tubular member to form the tubular member 202 as shown in FIG. 4. In other words, the first tubular member may be received within a lumen of the second tubular member to form the tubular member 202. The second tubular member may be fixedly attached to the first tubular member so that the position of the support segment 212a is fixed with respect to the tip 210. In other examples, the tubular member 202 may be formed as a unitary member or from any number of separate components joined to one another to form the tubular member 202. In one example, the second tubular member may include a balloon mounted on the first tubular member. The balloon may movable between a deflated configuration and an inflated configuration. In this manner, the outer diameter of the support segment may be adjustable (e.g., by inflating and/or deflating the balloon).

Figure 5:
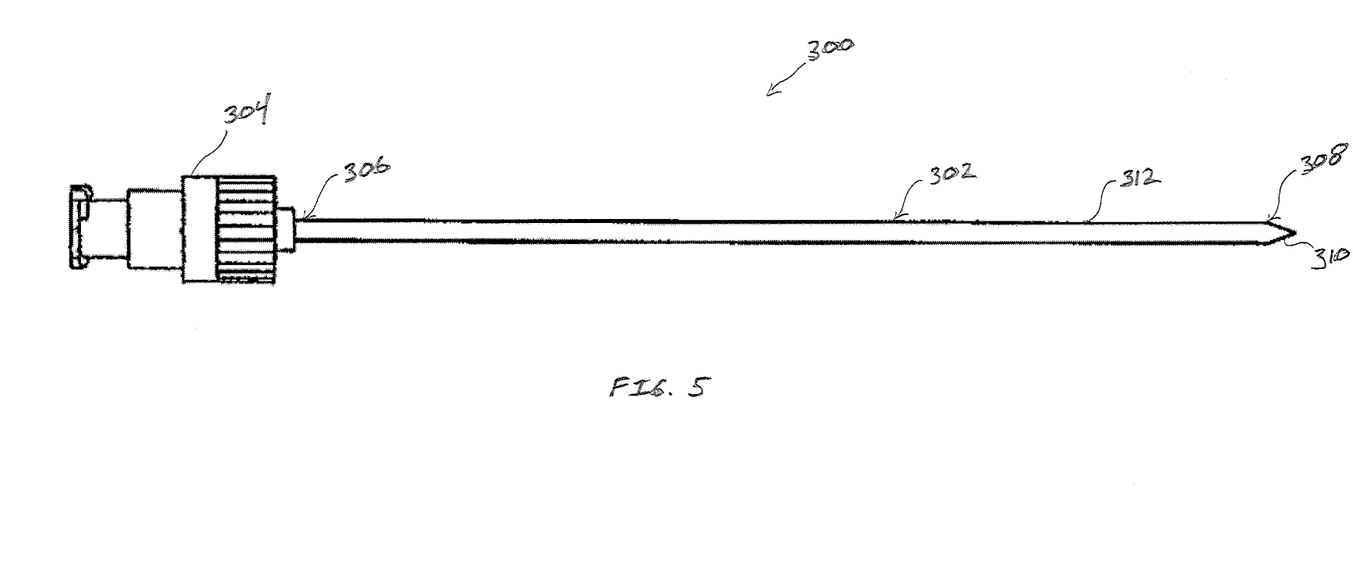
FIG. 5 illustrates one example of a needle.

FIG. 5 illustrates one example of the needle 300. The needle 300 may include an elongate shaft member 302. A hub 304 may be positioned at the proximal end of the needle 300. The shaft member 302 may include a proximal end 306 adjacent to the hub 304 and a distal end 308 positioned opposite the proximal end. The needle 300 may include a tip 310 positioned at the distal end 308. The needle 300 may include a body 312 extending proximally from the tip 310. In other words, the shaft member 302 of the needle 300 may include the body 312 and the tip 310 extending distally from the body 312. In one example, the shaft member 302 of the needle 300 may be substantially solid. In other words, the shaft member 302 may be configured as a substantially solid rod. In another example, a lumen may extend longitudinally within the needle 300. For example, the lumen of the needle 300 may extend from a proximal end opening at the hub 304 to a distal end opening at the tip 310. To that end, the shaft member 302 may be configured as a tubular member. A fluid (e.g., contrast media) may be introduced through the lumen of the needle and out the distal end opening at the tip 310 to track the progress of a medical procedure.

The shaft member 302 of the needle 300 may be received within the lumen of the support cannula 200 as shown in FIG. 1. In one example, the length of the shaft member 302 may be longer than the length of the support cannula 200 (e.g., the distance from the proximal end opening of the hub 204 to the distal end opening of the tip 210) and the length of the catheter 100. In this manner, the tip 310 of the needle 300 may be disposed outside of the catheter 100 as shown in FIG. 1. In other words, the shaft member 302 of the needle 300 may extend through the distal end opening of the support cannula 200 and the distal end opening of the catheter 100 so that the tip 310 is positioned distal of the tip 110 of the catheter as shown in FIG. 1. This may aid in advancing the tip 310 of the needle 300 and the tip 110 of the catheter 100 through a body tissue for percutaneous placement of the catheter as further described below. Additionally, or alternatively, the hub 304 of the needle 300 may be engaged with the hub 204 of the support cannula 200. In one example, the hub 304 of the needle 300 may be coupled to the hub 204 of the support cannula 200 to couple the needle and the support cannula to one another for delivery of the catheter 100 to the body cavity as described above with reference to the hub 204 of the support cannula 200 and the hub 104 of the catheter 100.

In any of the examples described herein, the catheter 100, the support cannula 200, and the needle 300 may be formed from any suitable material known in the art. In one example, the tubular member 102 of the catheter 100 may be formed from a flexible polymeric material such as, for example polyurethane (e.g., ULTRATHANE® from Cook Medical, Bloomington, Ind.), silicone, nylon, or any combination thereof. The tubular member 202 of the support cannula may be formed from a material having a greater stiffness than the tubular member 102 of the catheter 100. In one example, the tubular member 202 may be formed from stainless steel, nickel titanium alloy (e.g., nitinol), or any other suitable metallic material. The support segment 212a and the extension segment 212b may be formed from the same or different materials. In one example, the support segment 212a may be formed from polyvinyl chloride (PVC), nylon, polyether ether ketone (PEEK), stainless steel, or polytetrafluoroethylene (PTFE). Additionally, or alternatively, the extension segment 212b may be formed from stainless steel. The shaft member 302 of the needle 300 may be formed from any suitable polymeric or metallic material as described with respect to the tubular body 102 of the catheter 100 and/or the tubular body 202 of the support cannula 200. In other examples, the tubular member 102, the tubular member 202, and/or the shaft member 302 may be formed from polyurethane, silicone, nylon, polyamide, PVC, PEEK, PTFE, expanded polytetrafluoroethylene (ePTFE), polyethylene, stainless steel, nickel titanium alloy (e.g., nitinol), or any other suitable polymeric or metallic material. Additionally, or alternatively, the hub 104 of the catheter 100, the hub 204 of the support cannula, and/or the hub 304 of the needle 300 may be formed from a semi-rigid material such as a semi-rigid plastic material. In other examples, any portion of the catheter 100, the support cannula 200, and the needle 300 may be formed from any suitable material known in the art.

Figure 6:
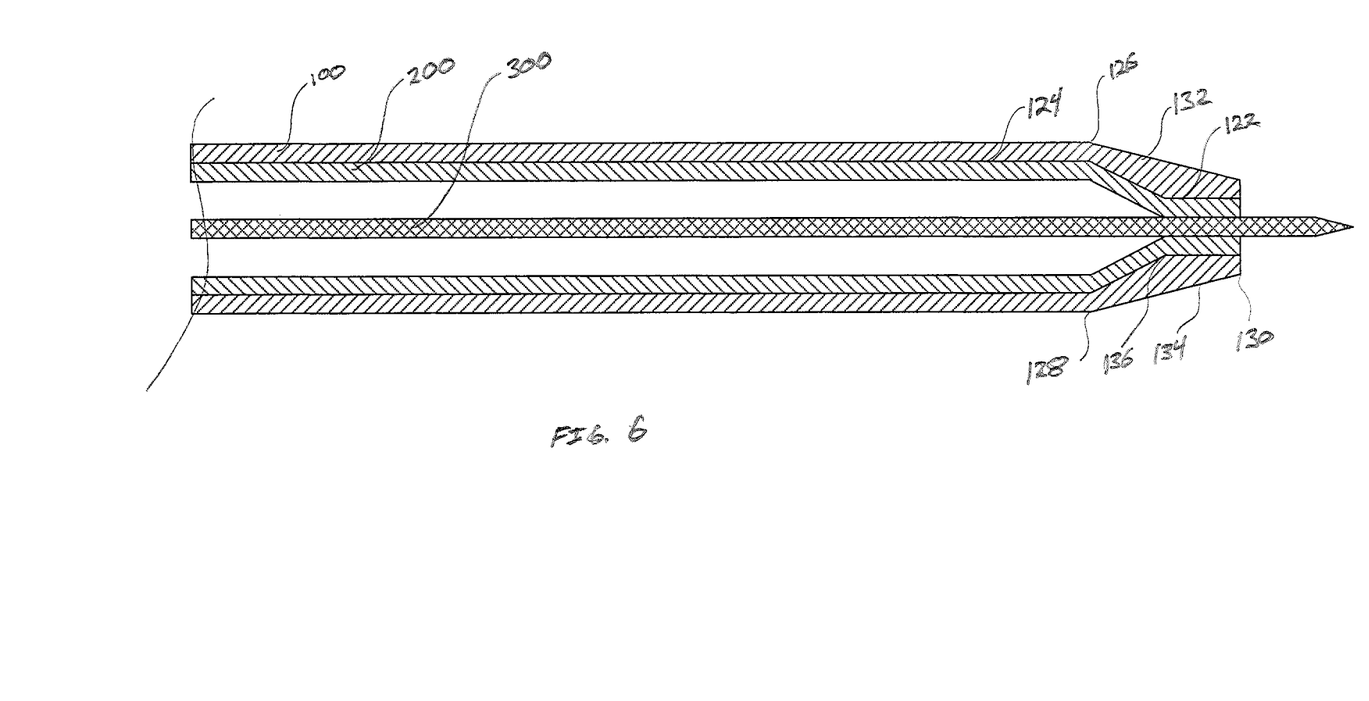
FIG. 6 is a longitudinal cross sectional view of a distal portion of the system of FIG. 1.

FIG. 6 is a longitudinal cross sectional view of the distal portion of the system shown in FIG. 1 including the catheter 100, the support cannula 200 received within the catheter, and the needle 300 received within the support cannula. The lumen of the catheter may include a tip portion 122 and a body portion 124. The tip portion 122 of the catheter lumen may be positioned within the tip 110 of the tubular member 102 of the catheter 100. The body portion 124 of the catheter lumen may be positioned within the body 112 of the tubular member 102 of the catheter 100. The tip portion 122 and the body portion 124 may be in fluid communication with one another to collectively define a substantially continuous lumen extending longitudinally within the tubular member 102 of the catheter 100.

In one example, the body 112 may include a distal end 126 as shown in FIG. 6. The tip 110 may include a proximal end 128 and a distal end 130 opposite the proximal end. The proximal end 128 of the tip 110 may be positioned adjacent to the distal end 126 of the body 112. The proximal end 128 of the tip 110 and the distal end 126 of the body 112 may be contiguous with one another so that the tip extends distally from the body as described above. The tip 110 and the body 112 may be formed as a unitary structure (e.g., by molding or extrusion) or as separate structures joined to one another (e.g. by bonding). The tip portion 122 of the catheter lumen may include a proximal end longitudinally aligned with the proximal end 128 of the tip 110 and a distal end longitudinally aligned with the distal end 130 of the tip. In other words, the tip portion 122 may extend longitudinally from the proximal end 128 of the tip 110 to the distal end 130 of the tip. Additionally, or alternatively, the body portion 124 of the catheter lumen may include a distal end longitudinally aligned with the distal end 126 of the body 112.

The catheter 100, with the support cannula 200 received within the catheter as shown in FIGS. 1 and 6, may be in a non-expanded or non-stretched configuration. In other words, the support cannula 200 may be positioned within the lumen of the catheter 100 without expanding or stretching the sidewall of the tubular member 102 of the catheter. For example, the catheter 100 and the support cannula 200 may be sized such that, upon introduction of the support cannula within the lumen of the catheter, the diameter of the catheter (e.g., the inner diameter of the body 112 and/or the inner diameter of the tip 110 as further described below) remains substantially unchanged.

In one example, a diameter of at least a portion of the tip portion 122 of the lumen of the catheter 100 may be smaller than a diameter of the body portion 124 of the lumen of the catheter. In other words, the tip 110 of the catheter 100 may have an inner diameter that is smaller than an inner diameter of the body 112 of the catheter. Additionally, or alternatively, the diameter of the body portion 124 of the lumen of the catheter 100 (i.e., the inner diameter of the body 112) may be substantially constant along the length of the body 112 extending from the proximal end of the body to the distal end 126 of the body. The diameter of the tip portion 122 of the catheter lumen (i.e., the inner diameter of the tip 110) may vary longitudinally along the length of the tip 110. For example, the tip portion 122 may have a first diameter at the proximal end 128 of the tip 110 and a second diameter at the distal end 130 of the tip. The first diameter may be larger than the second diameter. Additionally, or alternatively, the first diameter may be substantially equal to the diameter of the body portion 124 of the catheter lumen. The tip portion 122 may taper from the first diameter to the second diameter as shown in FIG. 6. In this manner, the lumen of the catheter 100 may taper from a larger diameter at the body portion 124 to a smaller diameter of the tip portion 122.

In one example, the tip 110 may include a tapered segment 132 and an end segment 134 positioned distal of the tapered segment. The tapered segment 132 may extend distally from the proximal end 128 of the tip 110 to an intermediate point 136 of the tip. The tapered segment 132 may have a tapered inner diameter as shown in FIG. 6. In other words, the inner diameter of the tip 110 may become increasingly smaller in a proximal to distal direction along the tapered segment 132. In one example, the inner diameter of the tip 110 may have a substantially uniform taper from the first diameter of the tip portion 122 at the proximal end 128 of the tip to the second diameter of the tip portion at the intermediate point 136 of the tip. The end segment 134 may extend distally from the tapered segment as shown in FIG. 6. In other words, the end segment 134 may extend distally from the intermediate point 136 of the tip 110. The end segment 134 may have a substantially constant inner diameter as shown in FIG. 6. In other words, the inner diameter of the end segment 134 may be substantially unvarying from the intermediate point 136 to the distal end 130 of the tip 110. In one example, the tip portion 122 of the catheter lumen may have a substantially cylindrical shape along the end segment 134.

In other examples, the tapered segment 132 or the end segment may be omitted. For example, the tapered segment 132 may be omitted such that the end segment 134 extends from the proximal end 128 to the distal end 130 of the tip 110. The inner diameter of the tubular member 102 may transition in a stepwise manner from the larger inner diameter of the body 112 to the smaller inner diameter of the tip 110. In another example, the end segment 134 may be omitted such that the tapered segment 132 extends from the proximal end 128 to the distal end 130 of the tip 110. The inner diameter of the tip 110 may taper from the proximal end 128 to the distal end 130 of the tip 110.

The support cannula 200 may be disposed within the lumen of the catheter 100 as shown in FIG. 6. The support cannula 200 may aid in strengthening the catheter 100 (e.g., by supporting or reinforcing the tubular member 102) and/or straightening the catheter to retain the catheter in the delivery configuration for percutaneous placement of the catheter as further described below. At least a portion of the support cannula 200 may be sized and shaped to correspond to the inner diameter of the tubular member 102 of the catheter 100. For example, at least a portion of the body 212 (e.g., the support segment 212a) of the support cannula 200 may have an outer diameter corresponding to the inner diameter of the body 112 of the catheter 100. In other words, the outer diameter of at least a portion of the body 212 of the support cannula 200 may be substantially equal to or slightly smaller than the inner diameter of the body 112 of the catheter 100. In one example, the support segment 212a of the body 212 may have an outer diameter corresponding to the inner diameter of the body 112 of the catheter 100. The support segment 212a of the body 212 may extend along substantially the entire length of the body 212 or along a portion of the length of the body 212 as described above with reference to FIGS. 3-4. The outer surface of the support segment 212a may be in abutting contact with the inner surface of the body 112 of the catheter 100 as shown in FIG. 6.

Additionally, or alternatively, the tip 210 of the support cannula 200 may have an outer diameter corresponding to the inner diameter of the tip 110 of the catheter 100. In other words, the outer diameter of at least a portion of the tip 210 of the support cannula 200 may be substantially equal to or slightly smaller than the inner diameter of the tip 110 of the catheter 100. In one example, the tapered portion 210a of the tip 210 of the support cannula 200 may be sized and shaped to correspond to the tapered segment 132 of the tip 110 of the catheter 100. Additionally, or alternatively, the end portion 210b of the tip 210 of the support cannula 200 may be sized and shaped to correspond to the end segment 134 of the tip 110 of the catheter 100. In this manner, the outer diameter of the tip 210 of the support cannula 200 may correspond to the inner diameter of the tip 110 of the catheter 100 along substantially the entire length of the tip 210 of the support cannula as shown in FIG. 6. This may enable the tip 210 of the support cannula 200 to support and/or straighten the tip 110 of the catheter 100 along substantially the entire length of the catheter tip.

In one example, the support segment 212a of the support cannula 200 may be positioned within the perforated segment 118 of the body 112 of the catheter 100. The support segment 212a may extend proximally from the tip 210 to at least the proximal end of the perforated segment 118 of the catheter 100. In other words, the proximal end of the support segment 212a may be longitudinally aligned with or positioned proximal of the proximal end of the perforated segment 118 of the catheter 100. This may enable the support segment 212a of the support cannula 200 to support the body 112 of the catheter 100 along substantially the entire length of the perforated segment 118.

The support cannula 200 may be received within the catheter 100 to retain the catheter in the delivery configuration. For example, the support cannula 200 may have a stiffness that is greater than a stiffness of the catheter 100. Additionally, or alternatively, the support cannula 200 may be substantially linear in a relaxed configuration. Introduction of the support cannula 200 into the lumen of the catheter 100 may cause the catheter to straighten into the delivery configuration. For example, introduction of the support cannula 200 into the lumen of the catheter 100 may cause the retaining segment 114 of the catheter to unroll from the deployed configuration shown in FIG. 2 to the delivery configuration shown in FIG. 1. The tip 210 of the support cannula 200 may be received within the tip 110 of the catheter 100 as described above. In this manner, introduction of the support cannula 200 into the lumen of the catheter 100 may cause the tip 110 of the catheter to straighten as shown in FIG. 1.

Additionally, or alternatively, the support cannula 200 may be received within the catheter 100 to support at least a portion of the catheter for placement within the body cavity. For example, the support cannula 200 may be in contact with the inner surface of the catheter 100 (e.g., along the perforated segment 118 of the body 112 and/or along the tip 110) as described above. The catheter 100 with the support segment 200 received therein may be stronger (e.g., may have a greater rigidity and/or column strength) than the unsupported catheter. Such greater strength may reduce the tendency of the catheter 100 to buckle in response to exertion of a longitudinal force on the catheter. Such a longitudinal force may be exerted on the catheter 100 during percutaneous placement of the catheter as described below.

In one example, the perforated segment 118 of the body 112 of the catheter 100 may be weaker (e.g., less rigid) than the remainder of the body 112. This may be caused by the apertures 116 disposed in the perforated segment of the body 112. In other words, the perforated segment 118 of the body 112 may be less rigid than an unperforated segment of the body 112. In one example, the support segment 212a of the support cannula 200 may extend longitudinally along substantially the entire length of the perforated segment 118 as described above. In this manner, the support segment 212a may provide support to the catheter 100 along substantially the entire length of the perforated segment 118. This may help to strengthen or reinforce the perforated segment 118, which may otherwise be weaker than the unperforated segment of the body 112 of the catheter 100. Additionally, or alternatively, the tip 210 of the support cannula 200 may be received within the tip 110 of the catheter 100 as described above. In this manner, the support cannula 200 may support the catheter 100 along substantially the entire length of the tip 110 of the catheter.

In one example, the support cannula 200 and the needle 300 may be disposed within the lumen of the catheter 100 as shown in FIGS. 1 and 6 to retain the catheter in the delivery configuration for percutaneous placement of the catheter 100. The hub 204 of the support cannula 200 may be engaged with the hub 104 of the catheter 100 as described above. In this manner, longitudinal translation of the support cannula 200 relative to the catheter 100 may be inhibited. Additionally, or alternatively, the hub 304 of the needle may be engaged with the hub 204 of the support cannula 200 as described above. In this manner, longitudinal translation of the needle 300 relative to the support cannula 200 may be inhibited. The tip 310 of the needle 300 may be passed through a body tissue (e.g., the patient's skin) to form a puncture in the body tissue. The needle 300, the support cannula 200, and the catheter 100 may be advanced distally until the tip 110 of the catheter contacts the body tissue. The needle 300, the support cannula 200, and the catheter 100 may be advanced further distally so that the tip 110 of the catheter enters the body tissue through the puncture. The tapered outer surface of the tip 110 of the catheter 100 may gradually dilate the puncture in the body tissue during introduction of the catheter through the body tissue. In other words, the puncture may be gradually enlarged by passage of the tip 110 of the catheter therethrough.

Once the tip 110 of the catheter 100 has been passed through the body tissue, the needle 300 may be retracted proximally relative to the support cannula 200 and removed from the lumen of the support cannula. The support cannula 200 and the catheter 100 may be advanced further distally until the retaining segment 114 of the catheter is positioned within the body cavity. The support cannula 200 may be retracted proximally relative to the catheter 100 and removed from the lumen of the catheter. To that end, the catheter 100 and/or the support cannula 200 may include a low friction material, which may reduce the friction between the catheter and the support cannula. The low friction material may include a non-stick material such as, for example, PTFE, sodium bicarbonate, a silicone lubricant, or any other biocompatible lubricant. In one example, the catheter 100 and/or the support cannula 200 may be formed from the low friction material. In another example, the catheter 100 and/or the support cannula 200 may include a layer of low friction material (e.g., along the inner surface of the catheter and/or the outer surface of the support cannula). In one example, the outer surface of the support segment 212a may include the low friction material. The low friction material may reduce the force that may be required to remove the support cannula from the catheter and/or prevent the support cannula and the catheter from sticking to one another.

Additionally, or alternatively, the support segment 212a of the support cannula 200 may include a balloon as described above. The balloon may be inflated to support the catheter 100 during percutaneous placement of the catheter as described above. Following placement of the catheter 100, the balloon may be deflated for removal of the support cannula 200 from the catheter. Deflating the balloon may reduce the frictional force between the support cannula 200 and the catheter 100 (e.g., by reducing the surface area of the support cannula which may be in contact with the catheter), which may aid in removing the support cannula from the catheter.

Upon removal of the support cannula 200 from the retaining segment 114, the catheter 100 may move toward the deployed configuration as described above. In other words, without the support cannula 200 disposed within the retaining segment 114 of the catheter, the loops (or other retaining mechanism) may be formed in the retaining segment as described above. This may prevent the catheter 100 from moving proximally out of the body cavity so that the catheter remains in place within the body cavity for drainage and/or infusion of fluid out of and/or into the body cavity.

In another example, a guide wire may be introduced through the body tissue (e.g., using the Seldinger technique) and advanced into the body cavity. The support cannula 200 may be disposed within the lumen of the catheter 100, and the needle 300 may be omitted. The support cannula 200 and the catheter 100 may be advanced distally over the guide wire to introduce the catheter through the body tissue and into the body cavity. In other words, the guide wire may be received within the lumen of the support cannula 200, and the support cannula and the catheter 100 may be advanced distally relative to the guide wire to introduce the catheter into the body cavity. The guide wire and the support cannula 200 may be retracted proximally and removed from the catheter 100 to enable the catheter to move to the deployed configuration as described above.

The support cannula 200 may strengthen the catheter 100 as described above to prevent the catheter from buckling or kinking (e.g., folding like an accordion) upon passage through the puncture in the body tissue. This may help to avoid damaging the catheter 100 upon introduction into the body cavity. Additionally, or alternatively, this may reduce the force required to pass the catheter 100 through the body tissue and/or improve the accuracy of the placement of the catheter. In other words, this may improve the ease of percutaneous placement of the catheter 100 (e.g., because the relatively smooth, unbuckled catheter body may be more effectively guided through the body tissue than a buckled or folded catheter body). Additionally, or alternatively, this may reduce the trauma experienced by the patient during placement of the catheter 100. For example, passage of the relatively smooth, unbuckled catheter body through the body tissue may be more comfortable for the patient compared to passage of a buckled catheter body (which may include ridges and/or folds) through the body tissue. In one example, the support provided by the support cannula 200 may enable the body 112 and/or the tip 110 of the catheter 100 to be formed from a relatively soft material (e.g., a low durometer polyurethane, silicone, nylon, or a blend of a polymeric material and an elastic material). In other words, because the catheter body may be supported by the support cannula, it may be unnecessary to form the catheter body from a relatively strong and/or stiff material. In one example, the body 112 and/or the tip 110 of the catheter 100 may be formed from a material having a durometer of less than about 95A, typically between about 90A and about 95A. In another example, the body 112 and/or the tip 110 of the catheter 100 may be formed from a material having a durometer of less than about 85A, typically between about 80A and about 85A. In another example, the body 112 and/or the tip 110 of the catheter 100 may be formed from a material having a durometer of less than about 80A, typically between about 70A and about 77A.

In one example, the outer diameter of the support segment 212a may correspond to the inner diameter of the perforated segment 118, the outer diameter of the tapered portion 210a of the tip 210 may correspond to the inner diameter of the tapered segment 132 of the tip 110; and the outer diameter of the end portion 210b of the tip 210 may correspond to the inner diameter of the end segment 134 of the tip 110 as shown in FIG. 6 and described above. In other words, the outer diameter of the support cannula 200 may correspond to the inner diameter of the catheter 100 along substantially the entire length of the perforated segment 118 of the body 112 and the tip 110. This configuration of the support cannula 200 may help to more effectively straighten the catheter 100 as compared to a conventional support cannula having a substantially cylindrical shape along the entire length of the cannula body. In this manner, the support cannula 200 may be configured to more effectively retain the catheter in the delivery configuration shown in FIG. 1 and/or strengthen the catheter.

In one example, a conventional support cannula may have a substantially cylindrical shape with an outer diameter corresponding to the inner diameter of the catheter body, which may be larger than the inner diameter of the catheter tip. In other words, the conventional support cannula may have a relatively large gauge size. When such a relatively large conventional support cannula is disposed within the catheter lumen, the support cannula may be unable to fit within the smaller diameter tip portion of the catheter lumen. Accordingly, the catheter tip may not be straightened or supported by the conventional support cannula. Not fully straightening the tip of the catheter may be problematic in that the physician may attempt to straighten the catheter tip by hand and potentially be punctured. Additionally, or alternatively, the needle may puncture through the sidewall of the catheter tip which may be curved and/or unprotected by the support cannula. Additionally, or alternatively, the curved catheter tip may be difficult to pass through the body tissue during percutaneous placement of the catheter.

In another example, a conventional support cannula may have a substantially cylindrical shape with an outer diameter corresponding to the smaller inner diameter of the catheter tip. In other words, the conventional support cannula may have a relatively small gauge size. When such a relatively small conventional support cannula is disposed within the catheter lumen, the support cannula may not be in contact with the inner surface of the perforated segment of the catheter body. In other words, there may be an annular space between the outer surface of the support cannula and the inner surface of the perforated segment of the catheter. The conventional support cannula may not support the perforated segment of the catheter body. This may enable the catheter body to buckle during percutaneous placement of the catheter.

Figure 7:
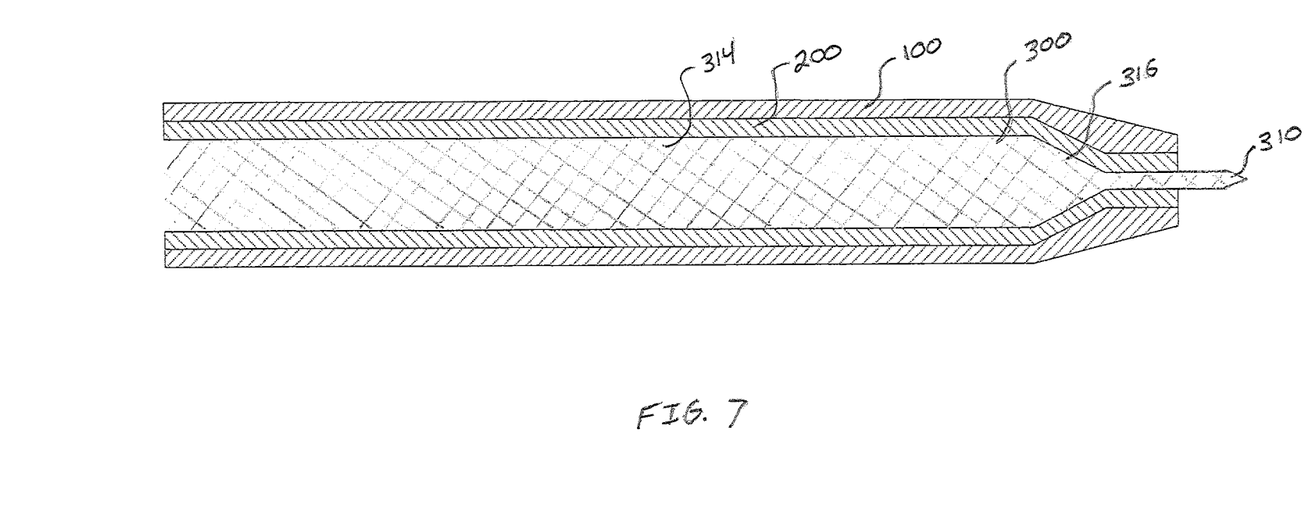
FIG. 7 is a longitudinal cross sectional view of a distal portion of another example of a system for draining a fluid from a body cavity and/or infusing a fluid into the body cavity including a catheter, a support cannula, and a needle.

FIG. 7 is a longitudinal cross sectional view of a distal portion of a system including the catheter 100, the support cannula 200 received within the catheter, and another example of the needle 300 received within the support cannula. In one example, the outer diameter of the needle 300 may vary longitudinally along the length of the needle as shown in FIG. 7. The needle 300 may include a first longitudinal segment 314 disposed within the body 212 of the support cannula and a second longitudinal segment 316 disposed within the tip 210 of the support cannula. The first longitudinal segment 314 of the needle 300 may have an outer diameter corresponding to the inner diameter of the body 212 of the support cannula 200. Additionally, or alternatively, the second longitudinal segment 316 of the needle 300 may have an outer diameter corresponding to the inner diameter of the tip 210 of the support cannula 200. To that end, at least a portion of the second longitudinal segment 316 may be tapered to correspond to the tapered portion 210a of the tip 210. Additionally, or alternatively, at least a portion of the second longitudinal segment 316 may have a substantially cylindrical shape to correspond to the end portion 210b of the tip 210. Additionally, or alternatively, the second longitudinal segment 316 may extend distally beyond the distal end of the support cannula 200 to the sharpened tip 310 of the needle 300.

In one example, the outer diameter of the needle 300 may correspond to the inner diameter of the support cannula 200 along substantially the entire length of the tubular member 202 of the support cannula. In this manner, the needle 300 may contact the inner surface of the support cannula 200 to provide support to the support cannula for percutaneous placement of the catheter 100. Additionally, or alternatively, the larger diameter of the first longitudinal segment 314 of the needle 300 compared to the second longitudinal segment 316 may help to prevent the support cannula 200 from moving proximally relative to the needle 300 during percutaneous placement of the catheter 100.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A system comprising:
   a catheter comprising an elongate tubular member comprising a proximal end, a distal end, a catheter lumen extending longitudinally within the catheter, a catheter body, and a catheter tip extending distally from the catheter body, the catheter tip comprising a tapered outer surface, wherein the catheter tip comprises a tapered segment and an end segment extending distally from the tapered segment, the tapered segment comprising an inner diameter that tapers from a first inner diameter that is substantially equal to an inner diameter of the catheter body to a second inner diameter that is smaller than the inner diameter of the catheter body, and the end segment comprises a substantially constant inner diameter that is substantially equal to the second inner diameter; and an elongate tubular support cannula slidably received within the catheter lumen and comprising a proximal end, a distal end, a cannula lumen extending longitudinally within the support cannula, a support segment disposed within the catheter body, and a cannula tip extending distally from the support segment and disposed within the catheter tip, the support segment comprising an outer diameter that is substantially constant along a length of the support segment and corresponds to the inner diameter of the catheter body, the cannula tip comprising a tapered portion and an end portion extending distally from the tapered portion, the tapered portion tapering from a first outer diameter that is substantially equal to the outer diameter of the support segment to a second outer diameter that is smaller than the first outer diameter and corresponds to the second inner diameter of the catheter tip, the end portion comprising a substantially constant outer diameter that is substantially equal to the second outer diameter of the cannula tip;

wherein the catheter body comprises a perforated segment comprising a plurality of apertures in fluid communication with the catheter lumen and longitudinally spaced from one another along a length of the perforated segment, and the support segment is disposed within the perforated segment of the catheter body and extends proximally from the cannula tip to at least a position longitudinally aligned with a proximal end of the perforated segment.

2. The system of claim 1, wherein the support segment comprises a substantially cylindrical shape, and the length of the support segment is greater than or equal to the length of the perforated segment of the catheter body.

3. The system of claim 1, wherein the support segment extends proximally from the cannula tip to at least a position longitudinally aligned with the proximal end of the tubular member of the catheter.

4. The system of claim 1, wherein the cannula tip comprises a first outer diameter that is substantially equal to the outer diameter of the support segment and a second outer diameter that is smaller than the first outer diameter and corresponds to the inner diameter of the catheter tip, and the cannula tip tapers from the first outer diameter to the second outer diameter.

5. The system of claim 1, further comprising an elongate needle slidably received within the lumen of the support cannula and comprising a proximal end, a distal end, and a sharpened tip positioned at the distal end of the needle.

6. A system comprising:
a catheter comprising an elongate tubular member comprising a proximal end, a distal end, a lumen extending longitudinally within the catheter, a tapered tip positioned at the distal end of the catheter, and a body extending proximally from the tip, the tip of the catheter comprising an inner diameter that is smaller than an inner diameter of the body of the catheter; and an elongate tubular support cannula slidably received within the lumen of the catheter and comprising a proximal end, a distal end, a lumen extending longitudinally within the support cannula, a tip positioned at the distal end of the support cannula and disposed within the tip of the catheter such that the tip of the support cannula does not extend distally beyond the distal end of the catheter, and a support segment extending proximally from the tip of the support cannula and disposed within the body of the catheter such that the body of the catheter remains in a non-stretched configuration, the tip of the support cannula comprising an outer diameter corresponding to the inner diameter of the tip of the catheter, the support segment comprising an outer diameter corresponding to the inner diameter of the body of the catheter, wherein the distal end of the support cannula is longitudinally aligned with the distal end of the catheter;

wherein the body of the catheter comprises a perforated segment comprising an aperture disposed in the catheter and in fluid communication with the lumen of the catheter, and the support segment of the support cannula extends from the tip of the support cannula to at least a position longitudinally adjacent to a proximal end of the perforated segment.

7. The system of claim 6, wherein the aperture comprises a plurality of apertures spaced from one another along a length of the perforated segment of the catheter body, and the support segment extends proximally from the tip of the support cannula to at least a position longitudinally aligned with a most proximal of the plurality of apertures.

8. The system of claim 6, wherein the catheter comprises a material comprising a durometer of less than about 95A.

9. The system of claim 6, further comprising an elongate needle slidably received within the lumen of the support cannula and comprising a proximal end, a distal end, and a sharpened tip positioned at the distal end of the needle.

10. The system of claim 9, wherein the sharpened tip of the needle is disposed distal of the tip of the catheter to puncture a body tissue.

11. The system of claim 6, wherein the aperture comprises a plurality of apertures spaced from one another along a length of the perforated segment of the catheter body.

12. The system of claim 11, wherein the plurality of apertures comprises a first set of apertures extending along the length of the perforated segment of the catheter body and a second set of apertures extending along the length of the perforated segment of the catheter body, and the first set of apertures and the second set of apertures are spaced from one another with respect to a circumference of the catheter body.

13. The system of claim 6, wherein a distal portion of the catheter comprises a retaining member, and the retaining member is movable between a delivery configuration and a retaining configuration to retain the catheter in place within a body cavity.

14. The system of claim 13, wherein, in the delivery configuration, the distal portion of the catheter is substantially linear, and, in the retaining configuration, the retaining member comprises at least one loop formed in the distal portion of the catheter.

15. The system of claim 13, wherein the retaining member is biased toward the retaining configuration so that, upon retraction of the support cannula relative to the catheter to remove the support cannula from the distal portion of the catheter, the retaining member moves to the retaining configuration.

* * * * *